United States Patent [19]

Rueb et al.

[11] Patent Number: 4,925,484
[45] Date of Patent: May 15, 1990

[54] N-PHENYLTETRAHYDROPHTHALIMIDES

[75] Inventors: Lothar Rueb, Speyer; Karl Eicken, Wachenheim; Hans J. Pander, Roedesheim-Gronau; Peter Plath, Frankenthal; Barbara Schwalge, Ludwigshafen; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 279,563

[22] Filed: Dec. 5, 1988

[30] Foreign Application Priority Data

Dec. 5, 1987 [DE] Fed. Rep. of Germany ....... 3741272

[51] Int. Cl.$^5$ .................. A01N 43/38; C07D 209/32; C07D 209/34; C07D 209/48
[52] U.S. Cl. ........................................... 71/96; 71/95; 71/74; 548/513; 548/465
[58] Field of Search ................... 548/513, 465; 71/95, 71/96, 74

[56] References Cited

FOREIGN PATENT DOCUMENTS 207894 1/1987 European Pat. Off. .
3603789 8/1987 Fed. Rep. of Germany ...... 548/513
8707602 12/1987 World Int. Prop. O. .

Primary Examiner—Johnnie R. Brown
Assistant Examiner—Frederick F. Tsung
Attorney, Agent, or Firm—Oblon, Spivak, McClelland, Maier & Neustadt

[57] ABSTRACT

N-Phenyltetrahydrophtalimides of the general formula I

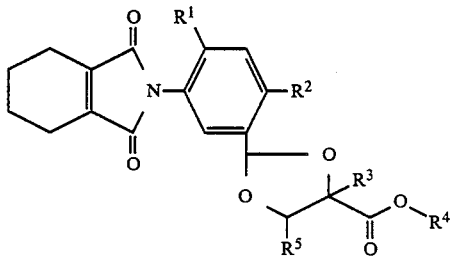

where $R^1$ is hydrogen or halogen, $R^2$ is halogen, $R^3$ is hydrogen or $C_1$-$C_4$-alkyl, $R^4$ is unsubstituted or $C_1$-$C_3$-alkoxy-substituted $C_1$-$C_8$-alkyl, $C_3$-$C_4$-alkenyl or $C_3$-$C_4$-alkynyl, and $R^5$ is hydrogen or $C_1$-$C_4$-alkyl, methods for their manufacture, and their use as herbicides.

4 Claims, No Drawings

N-PHENYLTETRAHYDROPHTHALIMIDES

N-Aryl-substituted tetrahydrophthalimides which have a herbicidal action are known. For example, EP-A-207,894 describes tetrahydrophthalimides of of the formula I'

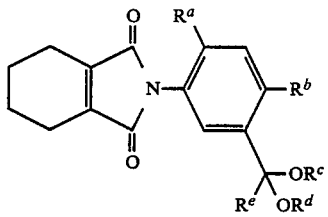

where the radicals have for example the following meanings:

$R^a$ and $R^b$ are identical or different and each is hydrogen or halogen;

$R^c$ and $R^d$ together denote, inter alia, a substituted or unsubstituted $C_2$-$C_3$-alkylene bridge; and $R^e$ is, inter alia, hydrogen, cyano or $C_1$-$C_4$-alkyl.

However, the action of these compounds is unsatisfactory at low application rates.

The object of the invention was therefore to provide N-phenyltetrahydrophthalimide compounds which have, at low application rates, a better action on unwanted plants without damaging crop plants.

We have now found that tetrahydrophthalimides of the formula I

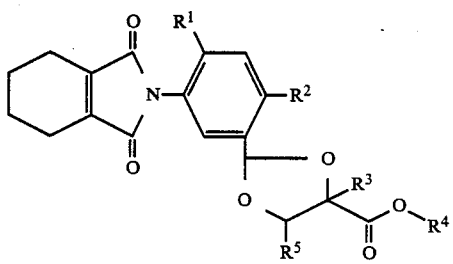

where $R^1$ is hydrogen or halogen, $R^2$ is halogen, $R^3$ is hydrogen or $C_1$-$C_4$-alkyl, $R^4$ is unsubstituted or $C_1$-$C_3$-alkoxy-substituted $C_1$-$C_8$-alkyl, $C_3$-$C_4$-alkenyl or $C_3$-$C_4$-alkynyl, and $R^5$ is hydrogen or $C_1$-$C_4$-alkyl, have an advantageous herbicidal action particularly when applied postemergence, and are selective in a number of crop plants.

By halogen, we mean fluorine, chlorine and bromine, halogen for $R^1$ preferably being fluorine and for $R^2$ preferably chlorine.

The term alkyl embraces straight-chain and branched radicals, e.g., methyl, ethyl, n-propyl and isopropyl.

The alkenyl and alkynyl radicals may also be straight-chain or branched. Examples of alkenyl radicals in formula I are 2-propenyl, 2-butenyl, 3-butenyl, and 2-isobutenyl, especially 2-propenyl and 2-butenyl; alkynyl radicals are usually propargyl, 2-butynyl and 3-butynyl.

The invention embraces the enantiomers, the diastereomers and mixtures thereof.

The N-substituted tetrahydrophthalimides are obtainable from 3,4,5,6-tetrahydrophthalic anhydride and an aniline of the formula V, e.g., in a solvent at a temperature of from 20° to 200° C., preferably 40° to 150° C. Suitable solvents are for example lower alkanoic acids such as glacial acetic acid or propionic acid, or aprotic solvents such as toluene or xylene in the presence of acidic catalysts such as aromatic sulfonic acids.

Preferred compounds I are those in which $R^1$ is hydrogen or fluorine, $R^2$ is chlorine, $R^3$ is $C_1$-$C_2$-alkyl, $R^4$ is $C_1$-$C_4$-alkyl, $C_3$-$C_4$-alkenyl or $C_3$-$C_4$-alkynyl and $R^5$ is hydrogen or methyl.

The anilines of the formula V are obtained for example by reducing a nitrobenzene IV having the appropriate acetal structure by means of reducing agents such as iron or tin(II) salts.

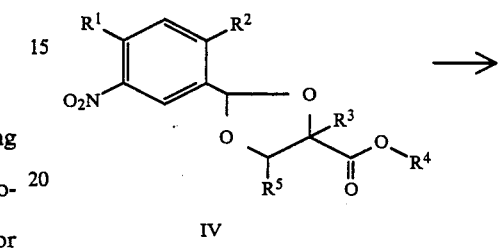

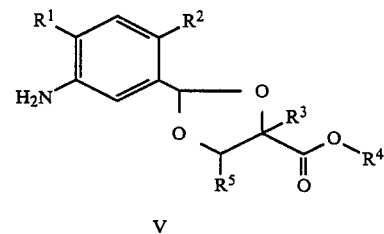

The reduction can also be carried out as a catalytic hydrogenation with a noble metal catalyst such as platinum or palladium, or with Raney nickel under relatively mild conditions.

Nitroacetals IV are accessible by reaction of an appropriate benzaldehyde II in an inert solvent in the presence of an acid with a diol of the formula III:

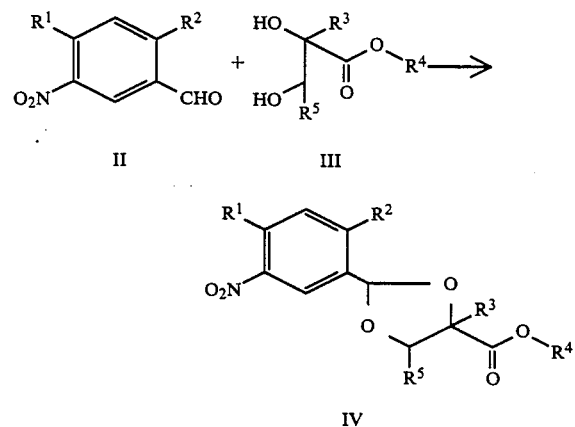

The recommendations given in the examples below were employed to obtain further compounds of the general formula I using different starting compounds. These compounds and their physical data are given in the following table. Compounds without any physical data may be obtained from the corresponding materials in analogous manner. Because of their close structural similarity to the manufactured and investigated compounds they are expected to have a similar action.

EXAMPLE

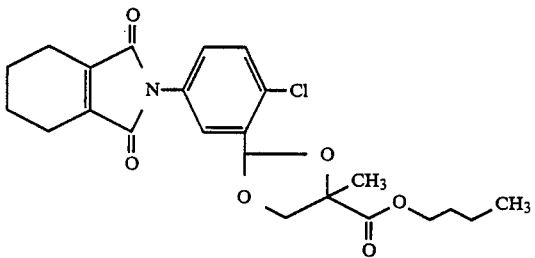

(a) 19.4 g of n-butyl 2,3-dihydroxyisobutyrate is added to 18.6 g of 2-chloro-5-nitrobenzaldehyde and 0.5 g of p-toluenesulfonic acid in 250 ml of toluene, and the mixture is refluxed for 5 hours using a water separator. The mixture is cooled, the solvent is removed and the remainder is dried in a high vacuum. There is obtained 35 g of 3-(5-methyl-5-n-butyloxycarbonyl-1,3-dioxolan-2-yl)-4-chloronitrobenzene (oil).

(b) While refluxing, 34.4 g of the above nitro compound in 20 ml of methanol is added to a mixture of 16.8 g of iron powder in 30 ml of methanol and 75 ml of glacial acetic acid. The mixture is refluxed for 2 hours. After cooling, 250 ml of water is added and the mixture is subjected to suction filtration. The filtrate is extracted three times, each time with 100 ml of ethyl acetate, dried, concentrated and dried in a high vacuum. There is obtained 31 g of 3-(5-methyl-5-n-butyloxycarbonyl-1,3-dioxolan-2-yl)-4-chloroaniline (oil).

(c) 15.7 g of the above aniline and 7.6 g of cyclohexene-1,2-dicarboxylic anhydride are refluxed for 5 hours in 150 ml of glacial acetic acid. After cooling, 150 ml of water is added, followed by extraction twice with 100 ml of methylene chloride, drying and removal of the solvent. The product is purified by chromatography and dried in a high vacuum. There is obtained 9.0 g of N-[3-(5-methyl-5-n-butyloxycarbonyl-1,3-dioxolan-2-yl)-4-chlorophenyl]-3.4.5.6-tetrahydrophthalimide (oil) (Table 1, no. 1.027).

Table 1 contains further examples of active ingredients which can be prepared by this synthesis principle.

TABLE 1

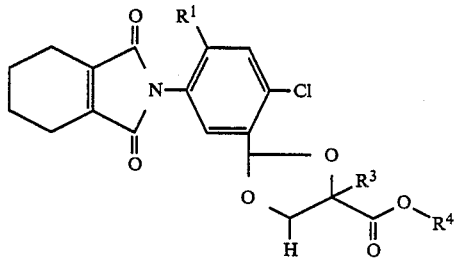

| No. | R¹ | R³ | R⁴ | mp [°C.] | IR [cm⁻¹] |
|---|---|---|---|---|---|
| 1.001 | H | H | $CH_3$ | | |
| 1.002 | F | H | $CH_3$ | | |
| 1.003 | H | $CH_3$ | $CH_3$ | oil | 1715, 1481, 1377, 1088 |
| 1.004 | F | $CH_3$ | $CH_3$ | | |
| 1.005 | H | $CH_2CH_3$ | $CH_3$ | oil | 2938, 1715, 1481, 1378, 1088 |
| 1.006 | F | $CH_2CH_3$ | $CH_3$ | | |
| 1.007 | H | H | $CH_2CH_3$ | | |
| 1.008 | F | H | $CH_2CH_3$ | | |
| 1.009 | H | $CH_3$ | $CH_2CH_3$ | oil | 1715, 1480, 1376, 1088 |
| 1.010 | F | $CH_3$ | $CH_2CH_3$ | oil | 1720, 1500, 1422, 1082 |
| 1.011 | H | $CH_2CH_3$ | $CH_2CH_3$ | oil | 2938, 1715, 1480, 1377, 1089 |
| 1.012 | F | $CH_2CH_3$ | $CH_2CH_3$ | oil | 1721, 1500, 1422, 1083 |
| 1.013 | H | H | $(CH_2)_2CH_3$ | | |
| 1.014 | F | H | $(CH_2)_2CH_3$ | | |
| 1.015 | H | $CH_3$ | $(CH_2)_2CH_3$ | oil | 2929, 1716, 1479, 1377, 1089 |
| 1.016 | F | $CH_3$ | $(CH_2)_2CH_3$ | oil | 1720, 1500, 1422, 1082 |
| 1.017 | H | $CH_2CH_3$ | $(CH_2)_2CH_3$ | oil | 2938, 1716, 1481, 1378, 1089 |
| 1.018 | F | $CH_2CH_3$ | $(CH_2)_2CH_3$ | oil | 1721, 1500, 1422, 1083 |
| 1.019 | H | H | $CH(CH_3)_2$ | | |
| 1.020 | F | H | $CH(CH_3)_2$ | | |
| 1.021 | H | $CH_3$ | $CH(CH_3)_2$ | | |
| 1.022 | F | $CH_3$ | $CH(CH_3)_2$ | | |
| 1.023 | H | $CH_2CH_3$ | $CH(CH_3)_2$ | | |
| 1.024 | F | $CH_2CH_3$ | $CH(CH_3)_2$ | | |
| 1.025 | H | H | $(CH_2)_3CH_3$ | | |
| 1.026 | F | H | $(CH_2)_3CH_3$ | | |
| 1.027 | H | $CH_3$ | $(CH_2)_3CH_3$ | oil | 2958, 1716, 1481, 1377, 1088 |
| 1.028 | F | $CH_3$ | $(CH_2)_3CH_3$ | oil | 2958, 1721, 1500, 1423, 1082 |
| 1.029 | H | $CH_2CH_3$ | $(CH_2)_3CH_3$ | oil | 2960, 1716, 1480, 1378, 1089 |
| 1.030 | F | $CH_2CH_3$ | $(CH_2)_3CH_3$ | oil | 2960, 1721, 1500, 1422 |
| 1.031 | H | $CH_3$ | $CH_2CH(CH_3)_2$ | oil | 2960, 1718, 1481, 1378, 1088 |
| 1.032 | F | $CH_3$ | $CH_2CH(CH_3)_2$ | | |
| 1.033 | H | $CH_2CH_3$ | $CH_2CH(CH_2CH_3)(CH_2)_3CH_3$ | oil | 2932, 1717, 1481, 1378, 1089 |
| 1.034 | F | $CH_2CH_3$ | $CH_2CH(CH_2CH_3)(CH_2)_3CH_3$ | | |

TABLE 2

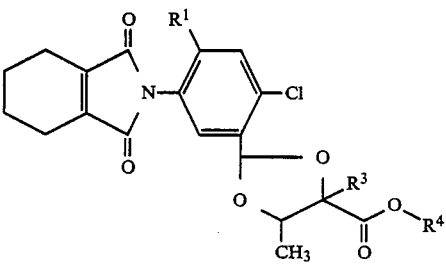

| No. | $R^1$ | $R^3$ | $R^4$ | mp [°C.] | IR [cm$^{-1}$] |
|---|---|---|---|---|---|
| 2.001 | H | CH$_3$ | CH$_3$ | | |
| 2.002 | F | CH$_3$ | CH$_3$ | | |
| 2.003 | H | CH$_3$ | CH$_2$CH$_3$ | | |
| 2.004 | F | CH$_3$ | CH$_2$CH$_3$ | | |
| 2.005 | H | CH$_3$ | (CH$_2$)$_2$CH$_3$ | | |
| 2.006 | F | CH$_3$ | (CH$_2$)$_2$CH$_3$ | | |
| 2.007 | H | H | CH(CH$_3$)$_2$ | oil | 2936, 1717, 1418, 1376 1101 |
| 2.008 | F | H | CH(CH$_3$)$_2$ | | |
| 2.009 | H | H | (CH$_2$)$_3$CH$_3$ | oil | 2958, 1715, 1480, 1378 1100 |
| 2.010 | F | H | (CH$_2$)$_3$CH$_3$ | | |
| 2.011 | H | H | CH$_3$ | oil | 1715, 1481, 1378, 1104 |
| 2.012 | F | H | CH$_3$ | | |
| 2.013 | H | H | (CH$_2$)$_2$CH$_3$ | | |
| 2.014 | F | H | (CH$_2$)$_2$CH$_3$ | | |

TABLE 3

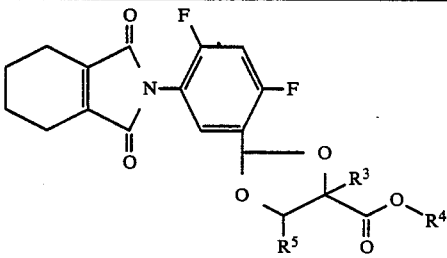

| No. | $R^3$ | $R^4$ | $R^5$ | mp [°C.] | IR [cm$^{-1}$] |
|---|---|---|---|---|---|
| 3.001 | H | CH$_3$ | H | | |
| 3.002 | CH$_3$ | CH$_3$ | H | | |
| 3.003 | H | CH$_3$ | CH$_3$ | | |
| 3.004 | CH$_3$ | CH$_3$ | CH$_3$ | | |
| 3.005 | H | CH$_2$CH$_3$ | H | | |
| 3.006 | CH$_3$ | CH$_2$CH$_3$ | H | | |
| 3.007 | H | CH$_2$CH$_3$ | CH$_3$ | | |
| 3.008 | CH$_3$ | CH$_2$CH$_3$ | CH$_3$ | | |
| 3.009 | H | (CH$_2$)$_2$CH$_3$ | H | | |
| 3.010 | CH$_3$ | (CH$_2$)$_2$CH$_3$ | CH$_3$ | | |
| 3.011 | H | (CH$_2$)$_2$CH$_3$ | CH$_3$ | | |
| 3.012 | CH$_3$ | (CH$_2$)$_2$CH$_3$ | CH$_3$ | | |
| 3.013 | H | CH(CH$_3$)$_2$ | H | | |
| 3.014 | CH$_3$ | CH(CH$_3$)$_2$ | H | | |
| 3.015 | H | CH(CH$_3$)$_2$ | CH$_3$ | oil | 2978, 1720, 1512, 1437, 1097, 1068 |
| 3.016 | CH$_3$ | CH(CH$_3$)$_2$ | CH$_3$ | | |
| 3.017 | H | (CH$_2$)$_3$CH$_3$ | H | | |
| 3.018 | CH$_3$ | (CH$_2$)$_3$CH$_3$ | H | oil | 1720, 1512, 1437, 1132 |
| 3.019 | H | (CH$_2$)$_3$CH$_3$ | CH$_3$ | | |
| 3.020 | CH$_3$ | (CH$_2$)$_3$CH$_3$ | CH$_3$ | | |

The herbicidal agents, or the active ingredients on which they are based, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.005 to 3.0, preferably 0.01 to 0.5, kg/ha.

The action of the active ingredients of the formula I on the growth of plants is illustrated in greenhouse experiments.

The vessels employed were plastic flowerpots having a volume of 300 cm$^3$ and filled with a sandy loam containing about 3.0% humus. The seeds of the test plants were sown separately, according to species.

For the postemergence treatment, either plants which had been sown in the pots and grown there were selected, or they were cultivated separately as seedlings and transplanted to the pots a few days before being treated.

Depending on growth form, the plants were grown to a height of from 3 to 15 cm before being treated with the active ingredients which were suspended or emulsified in water and sprayed through finely distributing nozzles. The application rate for postemergence treatment was 0.06 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments belonged to the following species:

| CODE | Botanical name | Common name |
|---|---|---|
| ABUTH | Abutilon theophrasti | velvet leaf |
| AMARE | Amaranthus spp. | pigweed |
| CHYCO | Chrysanthemum corinarium | crown daisy |
| DEDTO | Desmodium tortuosum | Florida beggarweed |
| GALAP | Galium aparine | catchweed bedstraw |
| IPOSS | Ipomoea spp. | morningglory |
| LAMAM | Lamium amplexicaule | henbit |
| MERAN | Mercurialis annua | annual mercury |
| POLPE | Polygonum persicaria | ladysthumb |
| SINAL | Sinapis alba | white mustard |
| SOLNI | Solanum nigrum | black nightshade |
| STEME | Stellaria media | chickweed |
| TRZAS | Triticum aestivum | spring wheat |
| TRZAW | Triticum aestivum | wheat |
| VERSS | Veronica spp. | speedwell |
| ZEAMX | Zea mays | Indian corn |

In view of the numerous application methods possible, the compounds according to the invention, or agents containing them, may be used in a large number of crop plants for removing unwanted plants. The following crops are examples:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |

| Botanical name | Common name |
| --- | --- |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the N-phenyltetrahydrophthalimides of the formula I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, etc.

It may also be useful to apply the N-phenyltetrahydrophthalimides of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 4

Herbicidal action of compound no. 1.027 on postemergence application of 0.06 kg/ha in the greenhouse

| Test plants | Damage (%) |
| --- | --- |
| ABUTH | 100 |
| AMARE | 100 |
| DEDTO | 100 |
| GALAP | 98 |
| IPOSS | 100 |
| MERAN | 100 |
| SOLNI | 100 |

TABLE 5

Herbicidal action and tolerance by a crop on postemergence application of 0.03 kg/ha of compound no. 1.027

| Test plants | Damage (%) |
| --- | --- |
| GALAP | 100 |
| LAMAM | 100 |
| MERAN | 100 |
| POLPE | 100 |
| SINAL | 95 |
| STEME | 100 |
| TRZAW | 0 |
| VERSS | 100 |

Examples demonstrating the control of unwanted broadleaved plants and tolerance by a crop on postemergence application of 0.03 kg/ha in the greenhouse.

TABLE 6

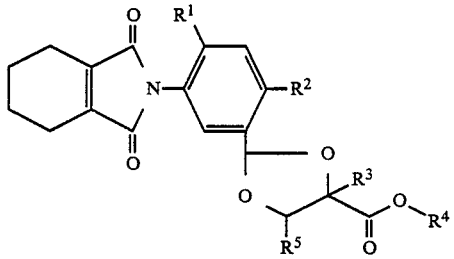

| Comp. no. | $R^1$ | $R^2$ | $R^3$ | $R^4$ | $R^5$ | TRZAS | CHYCO | SOLNI | GALAP | STEME |
|---|---|---|---|---|---|---|---|---|---|---|
| 2.007 | H | Cl | H | $CH(CH_3)_2$ | $CH_3$ | 10 | 100 | 100 | 100 | 90 |
| 2.009 | H | Cl | H | $(CH_2)_3CH_3$ | $CH_3$ | 10 | 100 | 100 | 100 | 100 |

TABLE 7

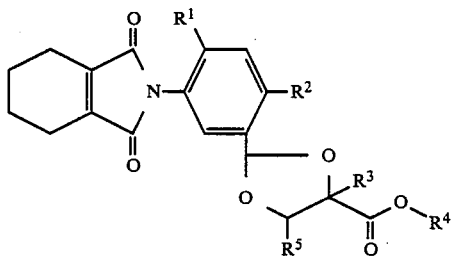

| Comp. no. | $R^1$ | $R^2$ | $R^3$ | $R^4$ | $R^5$ | ZEAMX | CHYCO | LAMAM | SOLNI | STEME |
|---|---|---|---|---|---|---|---|---|---|---|
| 1.031 | H | Cl | $CH_3$ | $CH_2CH(CH_3)_2$ | H | 0 | 100 | 100 | 100 | 100 |

TABLE 8

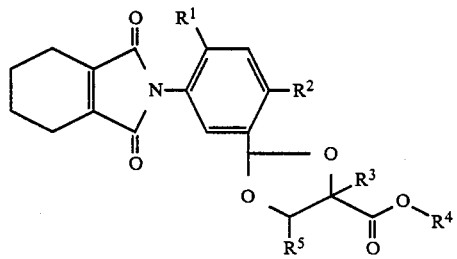

| Comp. no. | $R^1$ | $R^2$ | $R^3$ | $R^4$ | $R^5$ | TRZAS | CHYCO | SOLNI | VERSS |
|---|---|---|---|---|---|---|---|---|---|
| 1.005 | H | Cl | $CH_2CH_3$ | $CH_3$ | H | 10 | 100 | 100 | 100 |

We claim:
1. An N-tetrahydrophthalimide of the general formula

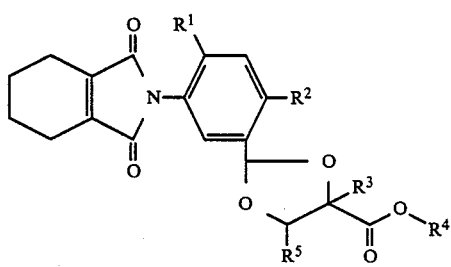

where $R^1$ is hydrogen or halogen, $R^2$ is halogen, $R^3$ is hydrogen or $C_1$–$C_4$-alkyl, $R^4$ is unsubstituted or $C_1$–$C_3$-alkoxy-substituted $C_1$–$C_8$-alkyl, $C_3$–$C_4$-alkenyl or $C_3$–$C_4$-alkynyl, and $R^5$ is hydrogen or $C_1$–$C_4$-alkyl, independently of the steric configuration.

2. A herbicidal agent containing a compound of the formula as set forth in claim 1, and conventional inert auxiliaries, extenders and diluents.

3. A process for combating the growth of unwanted plants, wherein a herbicidally effective amount of an N-tetrahydrophthalimide as set forth in claim 1 is allowed to act on the plants and their habitat.

4. An N-tetrahydrophthalimide of the general formula

11

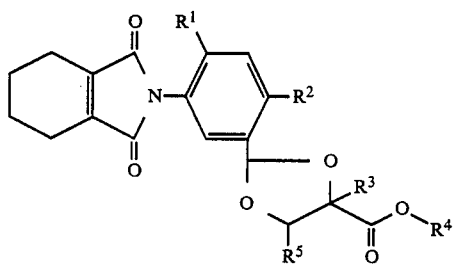

where $R^1$ is hydrogen or halogen, $R^2$ is halogen, $R^3$ is $C_1$–$C_4$-alkyl, $R^4$ is unsubstituted or $C_1$–$C_3$-alkoxy substituted $C_1$–$C_8$-alkyl, $C_3$–$C_4$-alkenyl or $C_3$–$C_4$-alkynyl, and $R^5$ is hydrogen or $C_1$–$C_4$-alkyl, independently of steric configuration.

* * * * *

12

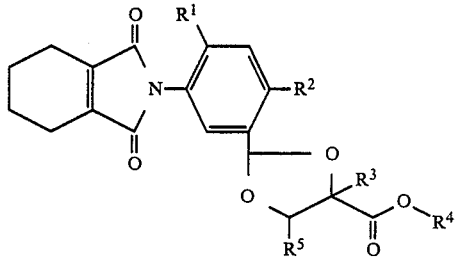

where $R^1$ is hydrogen or halogen, $R^2$ is halogen, $R^3$ is $C_1$–$C_4$-alkyl, $R^4$ is unsubstituted or $C_1$–$C_3$-alkoxy substituted $C_1$–$C_8$-alkyl, $C_3$–$C_4$-alkenyl or $C_3$–$C_4$-alkynyl, and $R^5$ is hydrogen or $C_1$–$C_4$-alkyl, independently of steric configuration.

* * * * *